(12) United States Patent
Siccardi et al.

(10) Patent No.: US 12,336,743 B2
(45) Date of Patent: Jun. 24, 2025

(54) POLYAXIAL SURGICAL SCREW AND DEVICE FOR IMPLANTING SAID SURGICAL SCREW

(71) Applicant: MEDACTA INTERNATIONAL SA, Castel San Pietro (CH)

(72) Inventors: Francesco Siccardi, Castel San Pietro (CH); Meinrad Fiechter, Castel San Pietro (CH); Marco Riva, Castel San Pietro (CH); Marco Rampon, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 628 days.

(21) Appl. No.: 17/602,224

(22) PCT Filed: Apr. 6, 2020

(86) PCT No.: PCT/IB2020/053261
§ 371 (c)(1),
(2) Date: Oct. 7, 2021

(87) PCT Pub. No.: WO2020/208496
PCT Pub. Date: Oct. 15, 2020

(65) Prior Publication Data
US 2022/0175426 A1 Jun. 9, 2022

(30) Foreign Application Priority Data
Apr. 8, 2019 (IT) .......................... 102019000005358

(51) Int. Cl.
*A61B 17/70* (2006.01)
*A61B 90/00* (2016.01)

(52) U.S. Cl.
CPC .......... *A61B 17/7085* (2013.01); *A61B 90/03* (2016.02); *A61B 2090/037* (2016.02)

(58) Field of Classification Search
CPC ............ A61B 17/7082; A61B 17/7085; A61B 17/7076; A61B 17/7091
See application file for complete search history.

(56) References Cited

U.S. PATENT DOCUMENTS 9,907,582 B1    3/2018 Olea
10,631,901 B2   4/2020 Fiechter et al.
(Continued)

FOREIGN PATENT DOCUMENTS

EP    2606841 A1    6/2013
EP    2801329 A2    11/2014
WO    2015/145343 A1    10/2015

OTHER PUBLICATIONS

International Search Report and Written Opinion issued in PCT/IB2020/053261, mailed Aug. 10, 2020, 13 pages.

*Primary Examiner* — Eduardo C Robert
*Assistant Examiner* — Anna V. Little
(74) *Attorney, Agent, or Firm* — Meunier Carlin & Curfman LLC

(57) ABSTRACT

Various implementations include a polyaxial surgical screw and a device for implanting the screw. The screw comprises: an internally hollow tulip displaying a first open end for accessing inside the tulip, a second end opposite to the first end, and a side wall extending between the first and the second end; and a threaded shank displaying a first end defining the tip of the screw and a second end opposite to the first one displaying a ball joint joined to the second end of the tulip to orient said shank with respect to the tulip itself. The tulip also comprises at least one elongated rod projecting from the side wall and extending from the first end in a direction opposite to the second end.

10 Claims, 10 Drawing Sheets

(56) References Cited

U.S. PATENT DOCUMENTS

| | | | |
|---|---|---|---|
| 2013/0103096 A1 | 4/2013 | Miller | |
| 2014/0277206 A1* | 9/2014 | Reitblat | A61B 17/708 |
| | | | 606/86 A |
| 2015/0148849 A1* | 5/2015 | Abidin | A61B 17/7091 |
| | | | 606/279 |
| 2015/0351810 A1* | 12/2015 | Lindner | A61B 17/7037 |
| | | | 606/278 |
| 2017/0079696 A1* | 3/2017 | Walker | A61B 17/7091 |
| 2018/0235677 A1* | 8/2018 | Kam | A61B 17/708 |
| 2018/0353223 A1* | 12/2018 | Otsubo | A61B 17/7082 |
| 2018/0353224 A1* | 12/2018 | Kam | A61B 17/7082 |

\* cited by examiner

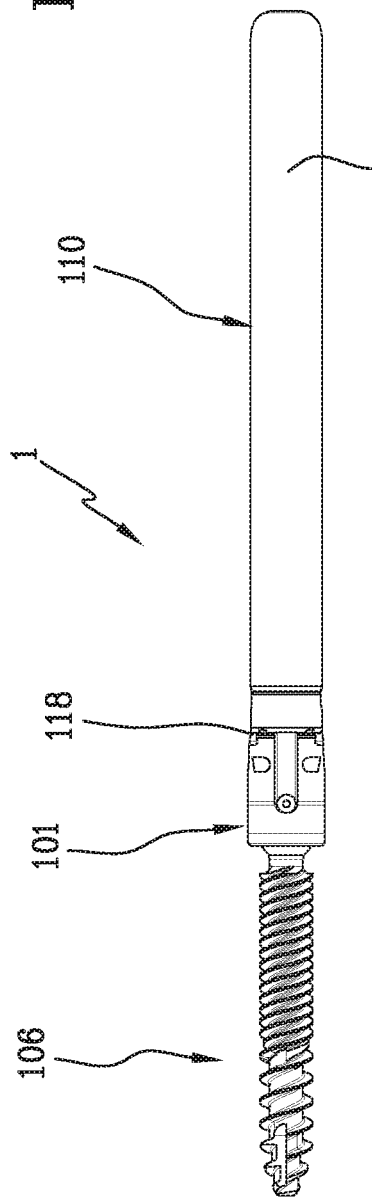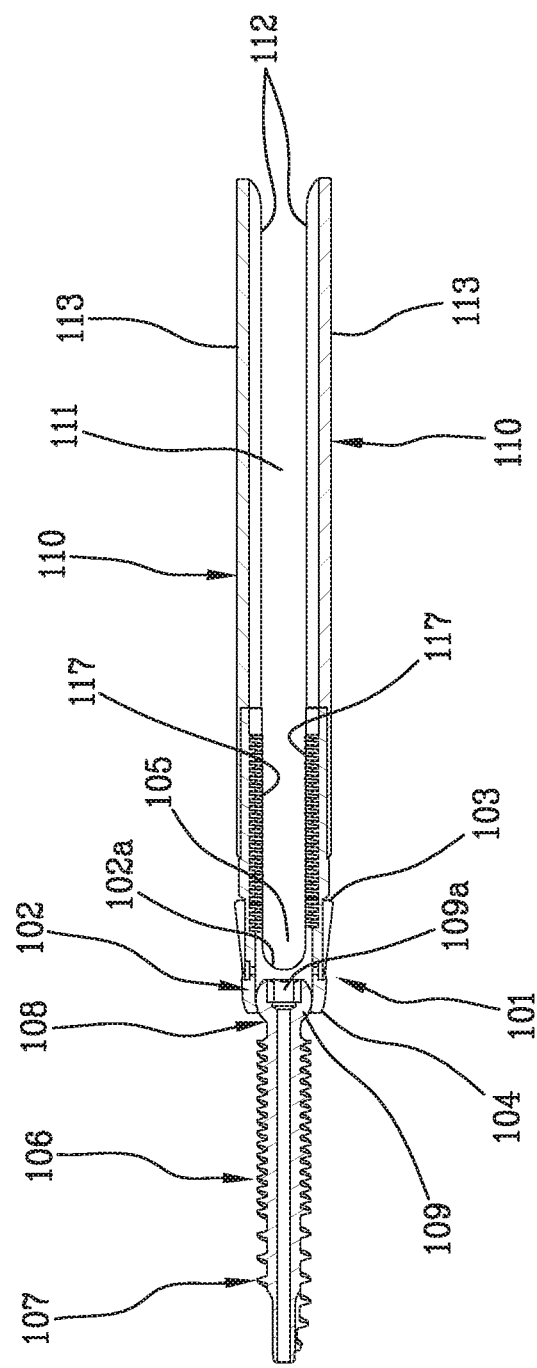

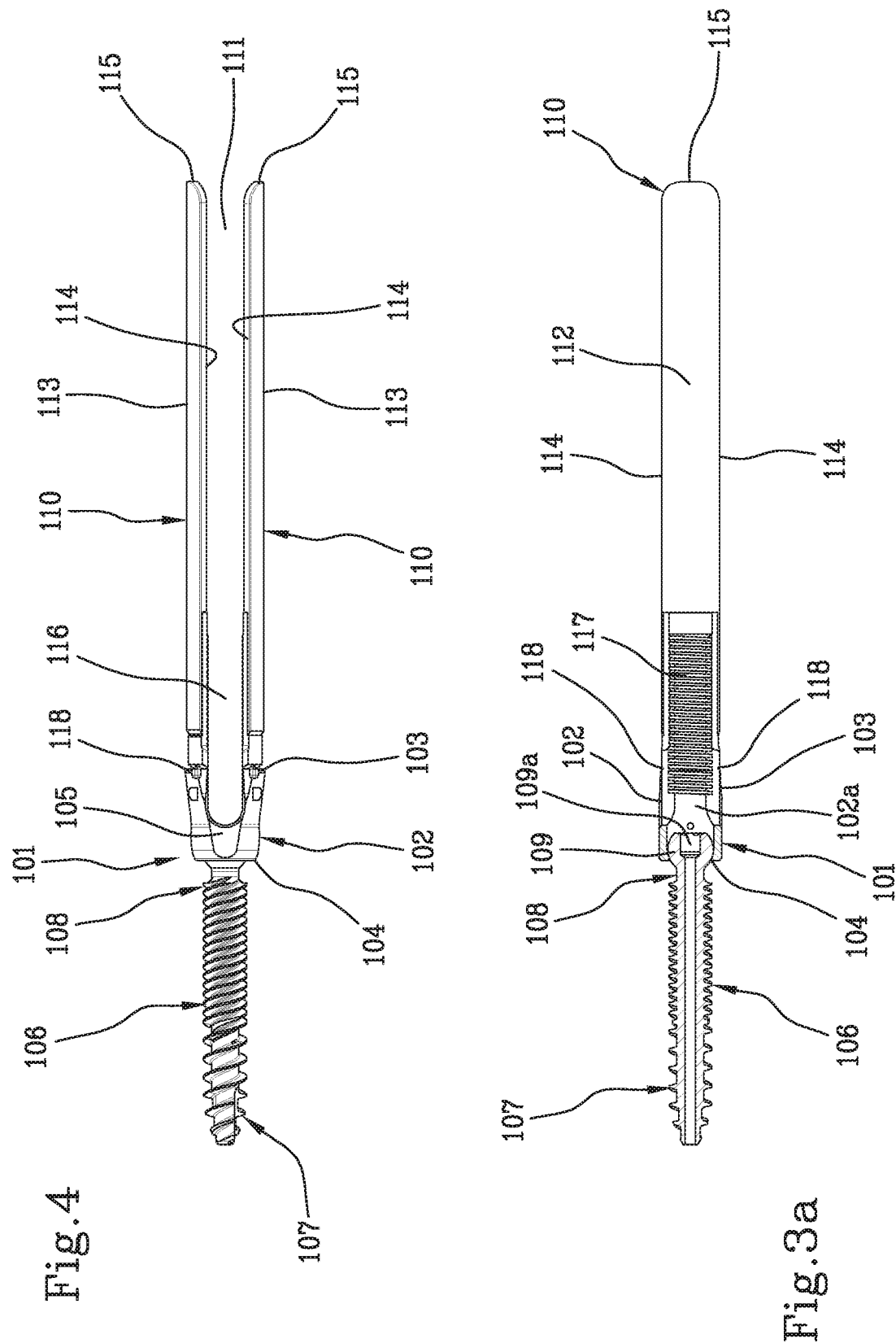

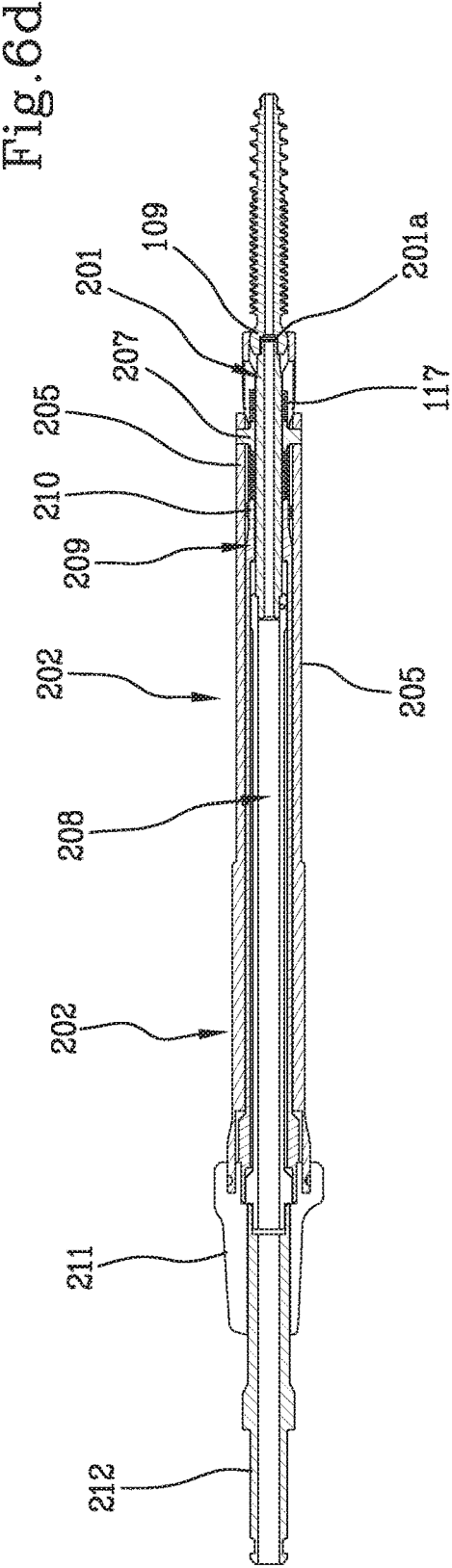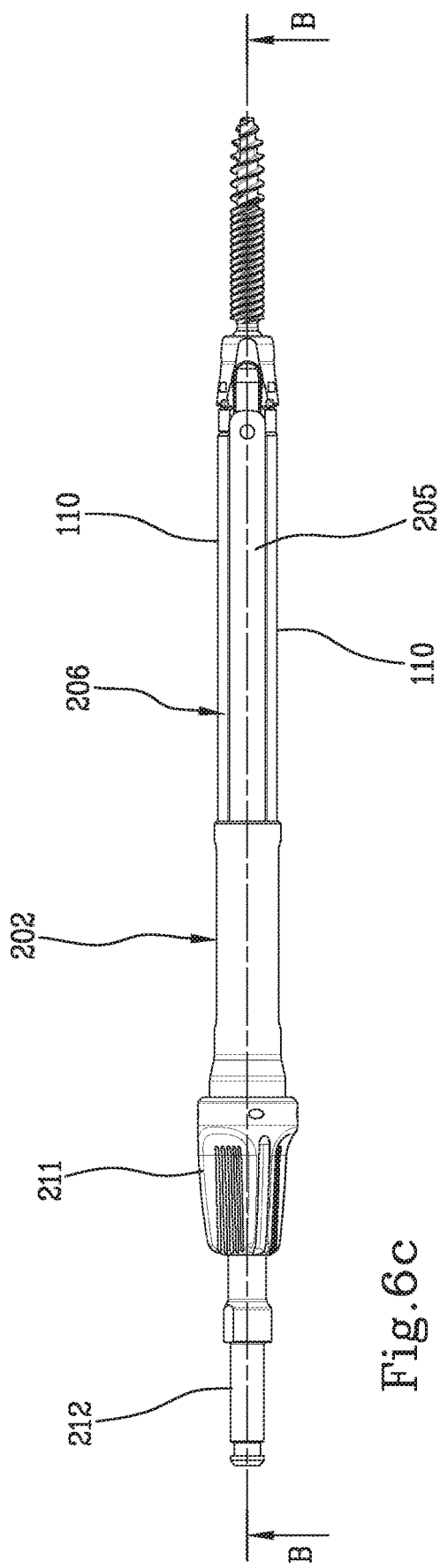

POLYAXIAL SURGICAL SCREW AND DEVICE FOR IMPLANTING SAID SURGICAL SCREW

This invention relates to a polyaxial surgical screw and a device for implanting this surgical screw.

Surgical operations on the spine, as known, frequently require the stabilisation of a portion of the spinal tract in order to facilitate the fusion of two or more vertebrae in a single bone agglomeration.

This type of procedure is frequently employed to correct many spinal pathologies such as, for instance, degenerative disc disease, scoliosis, spinal stenosis, and the like.

These corrective operations mostly require the use of implants, such as, in particular, bone grafts. Stabilising the spine permits bone growth in the intervertebral region; in this way a portion of the spine is fused into a single bone.

Over the years, stabilisation of the spine has been the subject of extensive research and various methods and devices have been developed to correct a large number of pathologies that are characteristic of this part of the anatomy in order to stabilise it, stimulating vertebral fusion at various levels.

One such system known in the prior art involves the insertion of a rod that is arranged longitudinally along the length of the spine in the region concerned. The rod is arranged according to the correct anatomy of that specific tract of a healthy spine.

With this method, the rod is, thus, arranged along the spine so as to engage a number of vertebrae, as required. Note that this type of surgical procedure usually involves the use of two parallel rods that are arranged at either side of the central part of the spine. Thus, during such surgical operations, the pair of rods is fixed to the spine using various fixing means, including, for example, screws suitably fixed to the bone structure, typically at the vertebral peduncle.

The angle of the rod and, thus, the position of the fixing screws, varies according to the type of correction required and obviously differs from one vertebra to another. The corrective rod and the screws used to secure the latter must clearly be properly inserted in order for the procedure to be successful.

In order to obtain a correct positioning of said elements, according to the patient's needs, polyaxial screws are used, which are thus able to work along transverse axes and not coinciding with the extension axis of the screw itself.

The implantation of said polyaxial screws, the rods, and any necessary fixing means typically requires invasive surgical procedures with subsequent lesions to the patient's skin and muscle tissue. This operation therefore usually requires fairly long periods of hospitalisation and rehabilitation.

To make the procedure less invasive, minimally invasive surgical techniques have been developed that considerably reduce surgical trauma. Such procedures have advantages for the patient, for instance, a shorter hospital stay, reduced post-operative pain, less rehabilitation, as well as for the hospital, in the form of shorter hospitalisation periods, lower costs, reduction in resources for rehabilitation. To meet the needs of this type of minimally invasive surgery, tools have been developed that enable the surgeon to fix said polyaxial screws in the desired position even through a small incision in the patient's body, and implant said rods in the desired position using said tools.

An example of this type of surgical tool is illustrated by the international patent application WO2015/145343 of the same applicant.

In this document, a tool to facilitate minimally invasive surgery procedures is made known, in particular for applying a polyaxial screw to anchor the above-mentioned rods.

Therefore, a first basically tubular body, called a "tulip", is provided that is equipped with a mechanical interlocking system at one end that is designed to interfere with the screw head.

In particular, the interlocking system consists of two end portions of the first tubular body, elastically deformable to engage, and disengage, corresponding openings formed on the outer surface of the tulip.

By inserting the tulip into the end of the tubular body, the end portions are then enlarged and deformed until the corresponding pins projecting from the end portions are inserted into the above-mentioned tulip openings. Subsequently, a second tubular body is fitted in the first tubular body to lock the two end portions and hold them abutted against the outer surface of the tulip.

In addition, the second tubular body has a groove that can be engaged to a protuberance emerging from the outer surface of the first tubular body to define a rotational bond between the two bodies. In other words, the second tubular body is integral with the first body in order to move the screw in any direction and position it correctly in the area of the vertebra where it is to be implanted.

In addition, the hollow structure of the tubular bodies enables the insertion of a screwdriver that, when inserted into the head, enables the threaded tip to rotate. In this situation, it should be noted that the two tubular bodies can be oriented by the operator, without changing the positioning of the threaded tip of the screw. In other words, the screw is polyaxial thanks to the coupling between the spherical head and the tulip.

Therefore, the surgical operation is as minimally invasive as possible, enabling the operator to insert the two tubular bodies through the micro-incisions made on the patient's body and still enabling the screw to be positioned correctly in relation to the vertebra.

However, the prior art solutions described above have some drawbacks.

In fact, it should be noted that the coupling between the tulip and the first tubular portion does not guarantee a particularly stable bond, especially during tilting and rotation.

In particular, the bond created by the elastic portions, although resistant and stable to axial stresses (along the longitudinal axis of the tubular bodies) leads to decoupling when subjected to very high rotational and shear stresses.

These stresses occur during the insertion of the reinforcement rod inside the tulip. In this case, in fact, the operator must align the side openings of the tulip with the direction in which the rod is inserted and must tilt the tulip into the correct position in relation to the threaded shank inserted into the vertebra. This operation results in shear stress generated by the tilting of the tulip in relation to the threaded shank of the screw. In this situation, the operator is, thus, obliged to extract the entire device from the patient's body to correctly re-couple the polyaxial screw to the first tubular body. This accidental decoupling of the screw from the tubular body could, in some cases, result in accidental injury to the patient and in the incorrect positioning of the surgical screw with consequences that could undermine the success of the operation.

In addition to the small size of the incision in the patient's body, the difficulty of this operation is also due to the presence of bodily fluids, such as blood, that impede the surgeon's visibility at the operating site, with the risk of surrounding soft tissue being "pinched" during the coupling of the tools.

An additional significant drawback of the known solution described above is that the operations involving assembling the screw with the first and second tubular body are particularly complex and require a certain manual dexterity on the part of the surgeon.

It should be noted that the step for inserting the tulip into the first tubular body must be performed with a certain force by the operator to enable the elastic portions to be deformed. Moreover, in this operation, the operator must ensure that the screw is correctly oriented in relation to the elastic portions in order to correctly insert the pins into the seats. However, the very small size of the surgical screws, derived precisely from the need to perform an operation as minimally invasive as possible, makes the handling and the correct and precise positioning of the screw in relation to the first tubular body, particularly complicated.

In addition, the insertion of the second tubular portion around the first one also entails additional laboriousness of use in order to implement the devices known in the state of the art.

The aim of the present invention is to overcome the drawbacks discussed above.

One purpose of this invention is to provide a polyaxial surgical screw that can be stably coupled to, and decoupled from, a corresponding screw implant device. In greater detail, one purpose of this invention is to provide a device and a screw that can be reliably joined to each other and, thus, able to maintain a stable coupling even when subjected to torsion, rotation, buckling, and tensile stress.

An additional purpose of this invention is to make available a surgical screw that can be easily and quickly coupled to the corresponding screw implant device.

Another purpose of this invention is to remove from the patient's body the operations involving the mechanical coupling of the devices, moving them away from the soft tissues during said operations.

An additional purpose of this invention is to provide a device as specified and a surgical screw that can be used easily and quickly, has a robust structure, and is conveniently priced.

In light of these purposes, this invention provides a polyaxial surgical screw and a device for implanting this screw, the characteristics of which are set out in the independent claims.

Further advantageous characteristics are set out in the dependent claims. All of the claims are cited in full in this document.

This invention will now be described in greater detail, with reference to the attached drawings provided merely by way of example, in which:

FIGS. 3 and 4 show respective, side elevation views of the polyaxial screw in FIGS. 1 and 2;

Figure 5:
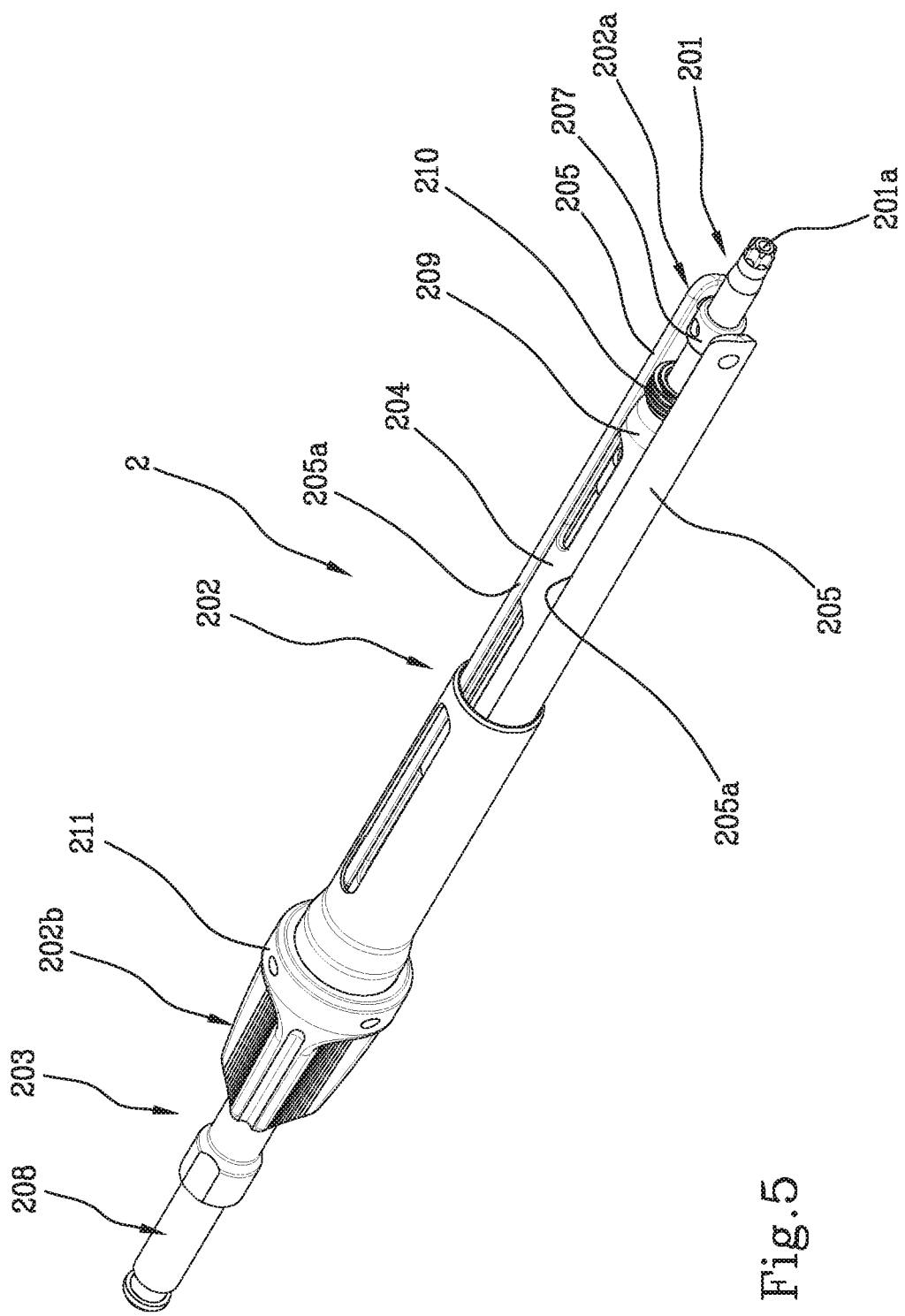
Figure 6A:
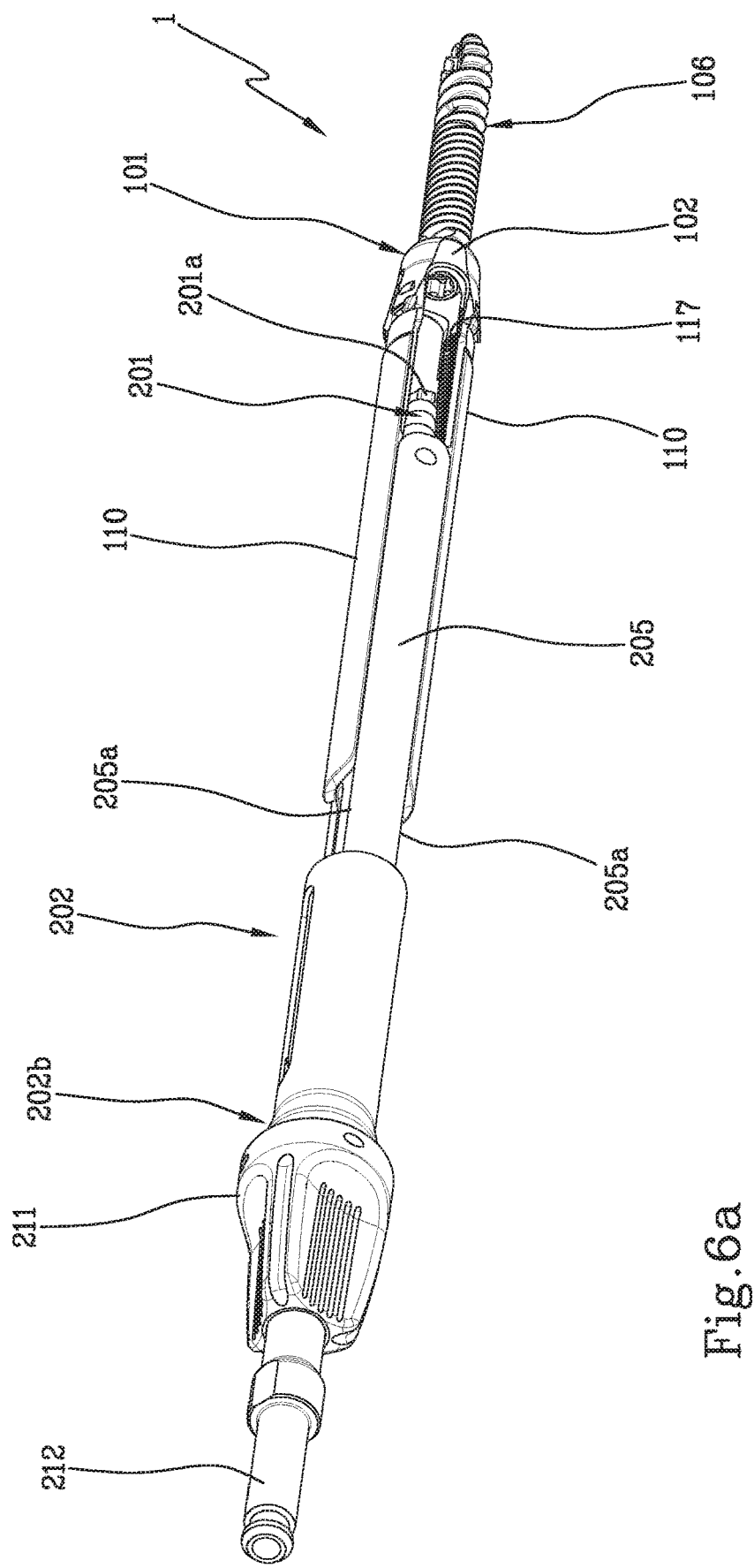
Figure 6B:
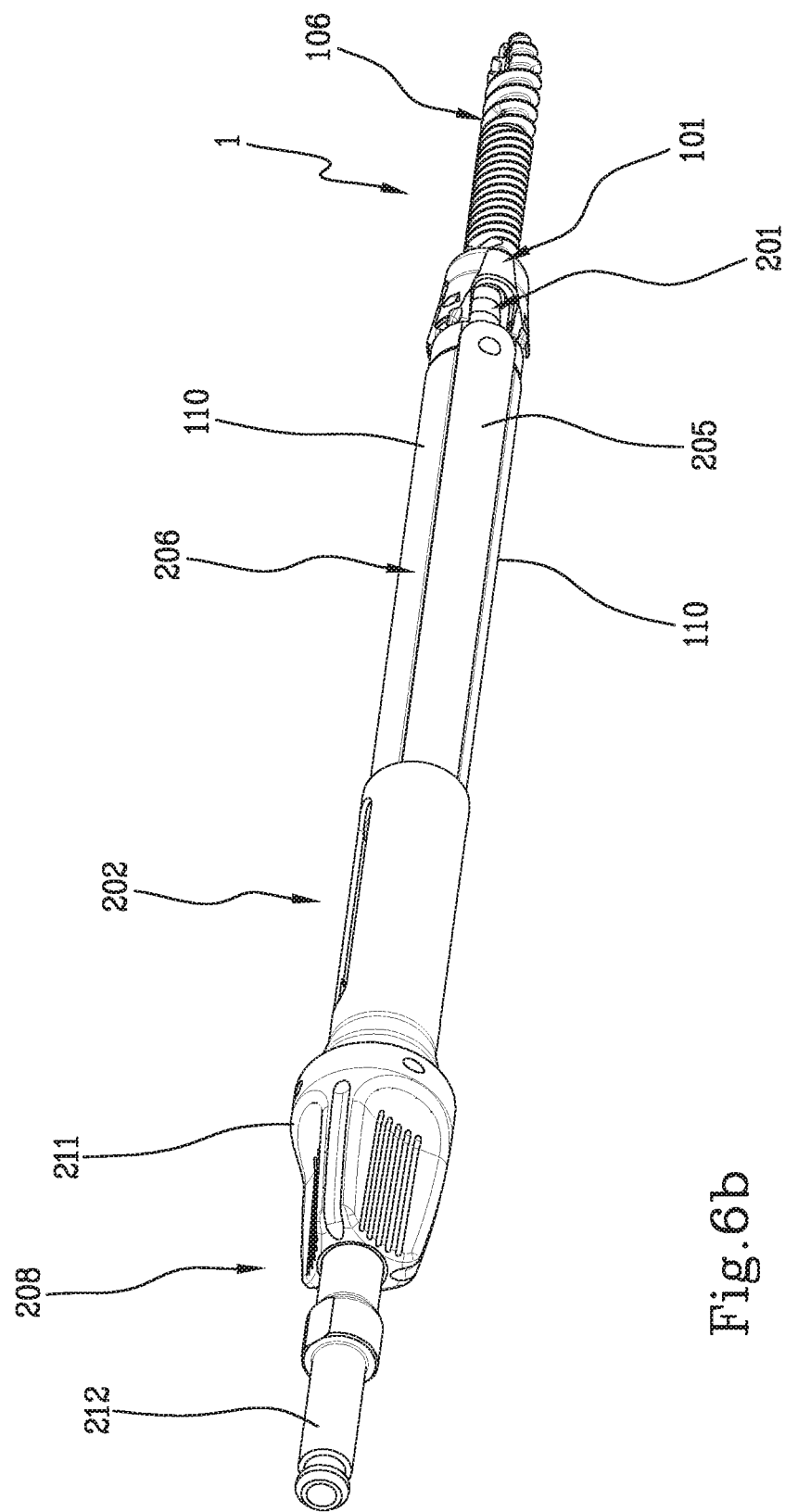
Figure 7A:
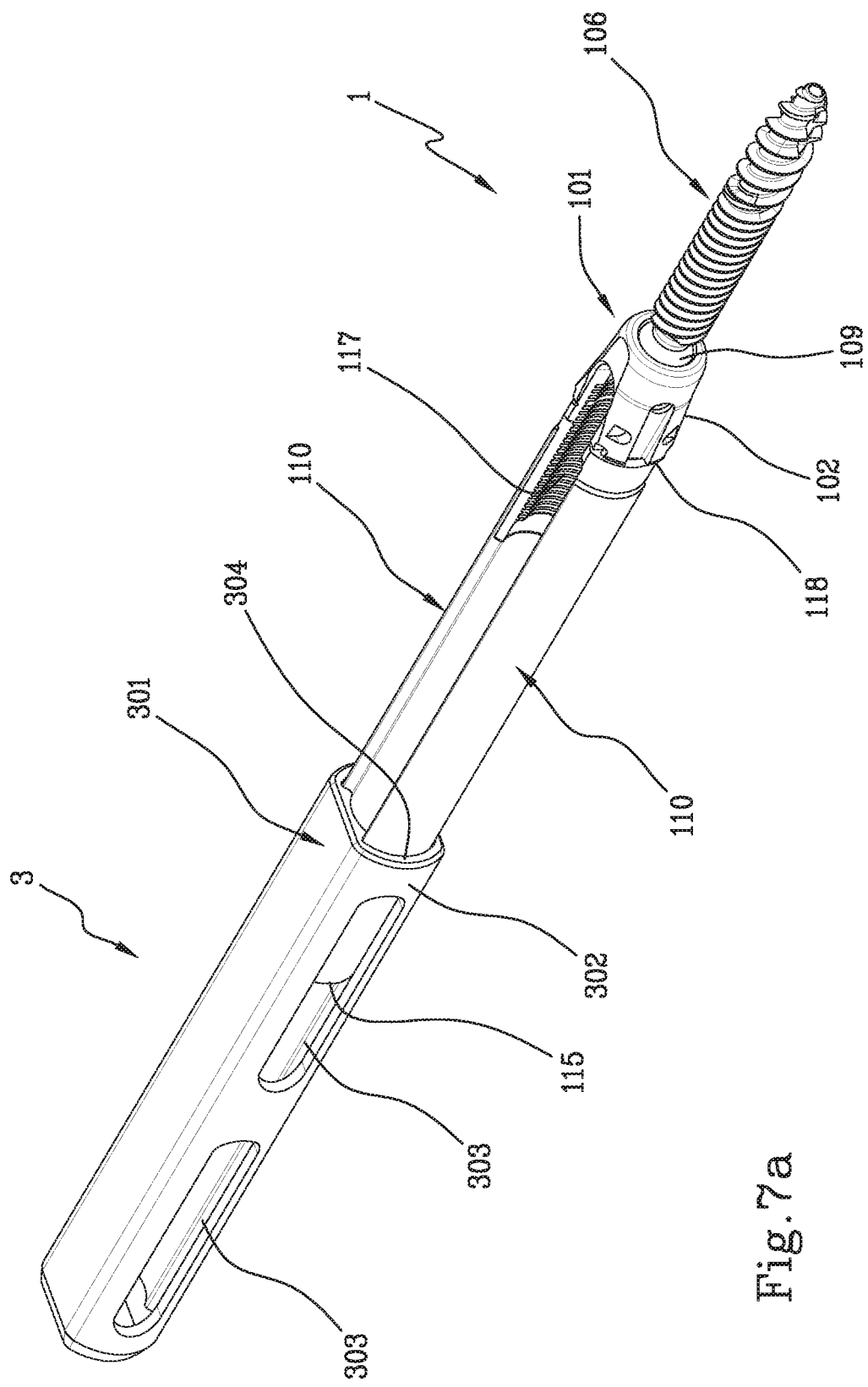
Figure 7B:
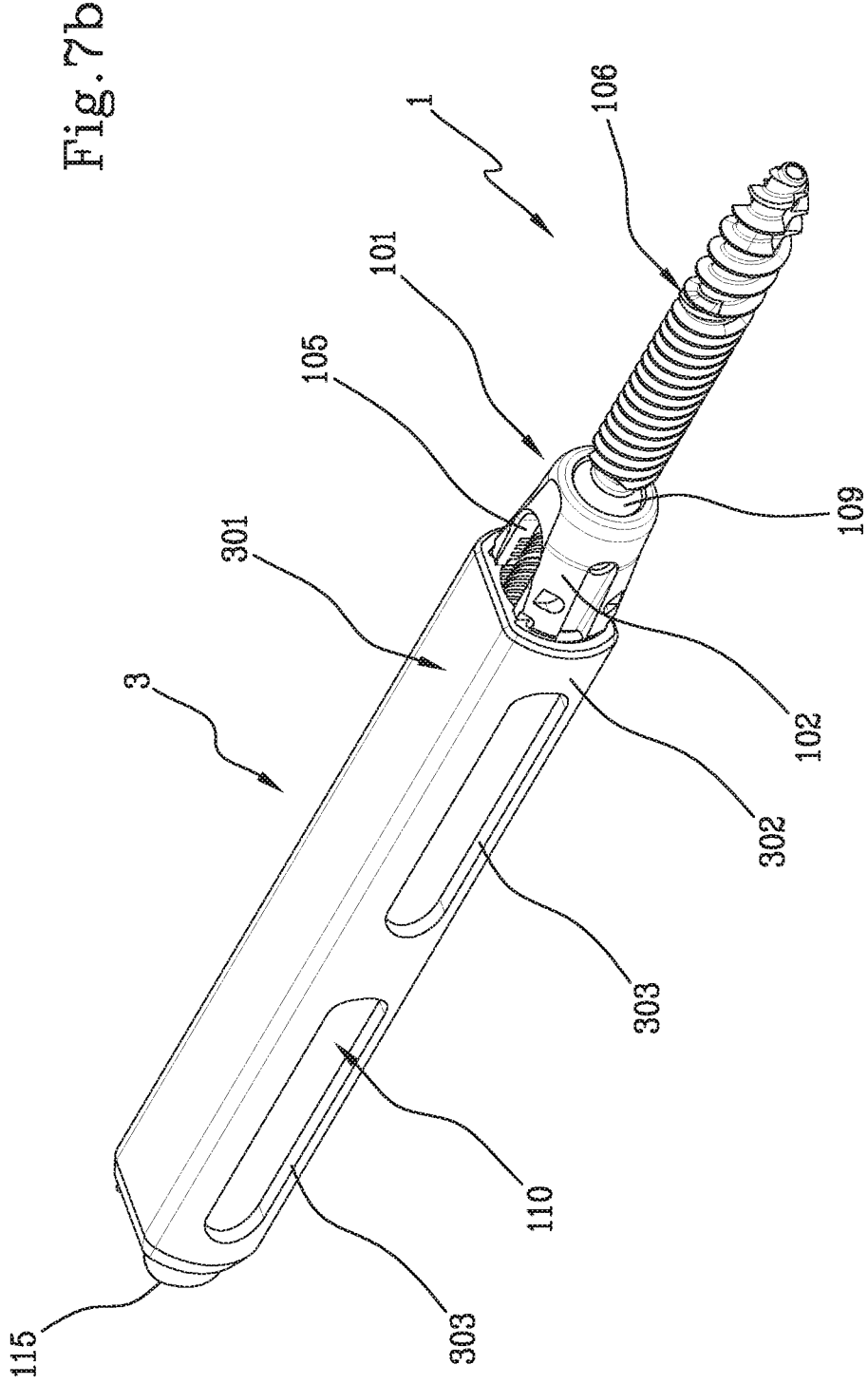

FIGS. 3*a* and 4*a* are longitudinal section views of the polyaxial surgical screw according to the invention and in accordance with views 3 and 4;

FIG. 5 shows a perspective view of an implant device for the screw illustrated in the figures above;

FIGS. 6*a* and 6*b* show perspective views of the device in FIG. 5 in two respective steps of coupling to the corresponding polyaxial surgical screw;

FIG. 6*c* shows a side elevation view of the device in coupling to the screw as illustrated in FIG. 6*b*;

FIG. 6*d* shows a longitudinal section view along the path B_B of the device illustrated in FIG. 6*c*;

FIGS. 7*a* and 7*b* show perspective views of a retaining element in two respective steps of coupling to the corresponding polyaxial surgical screw.

With reference to the figures listed above, the reference number 1 indicates, as a whole, a polyaxial surgical screw, which is the subject of this invention. The reference number 2, in contrast, indicates a device for implanting the surgical screw 1, which is also the subject of this invention. This invention also relates to a kit for implanting the screw 1 comprising the device 2 and a retaining element 3 of the screw 1, which is better described later in this discussion.

With particular reference to FIGS. 1 to 4, the polyaxial surgical screw 1 comprises an internally hollow tulip 101 that is defined by a "cup"-shaped side wall 102.

In other words, the side wall 102 has a basically truncated cone shape, and extends from a first open end 103 for accessing inside the tulip 101 to a second end 104 opposite the first. The second end 104 is also open and smaller than the access section of the first end 103. In this configuration, the side wall 102 is preferably tapered and converging towards the second end 104.

The tulip 101 also comprises two through openings 105 formed on the side wall to house a corrective rod (not illustrated in the attached figures since it is not part of this invention) inside the tulip 101 itself.

In particular, the two openings 105 are arranged on opposite sides to enable the rod to pass through the tulip 101 and along a direction perpendicular to the longitudinal extension of the side wall 102.

The openings 105 extend up to the first end 103 to interrupt the side wall 102 at the first access end 103.

The screw 1 also comprises a threaded shank 106 with a first end 107 defining the tip of the screw, designed to be inserted into the bone tissue. On the opposite side of the first end 107, a second end 108 extends that is equipped with a spherical head or ball joint 109 inserted into the second end 104 of the tulip 101. The ball joint 109 enables the shank 106, and its corresponding longitudinal extension axis, to be oriented in relation to the tulip 101.

The tulip 101 also advantageously comprises at least one elongated rod 110 projecting from the side wall 102 and extending from the first end 103 in the opposite direction to the second end 104.

The tulip preferably comprises two elongated rods 110, that are parallel and spaced apart from each other. The rods 110 define a channel 111 between them that is in communication with the first end 103 for accessing inside the tulip 101.

In more detail, each rod 110 has a "C"-shaped cross-section in which an concave inner surface 112 opposite a convex outer surface 113 is defined. The inner faces 112 face each other and define the above-mentioned channel 111. The outer surfaces 113 lie along the same cylindrical extension plane with a circular cross-section.

In addition, each rod 110 has two longitudinal edges 114 extending from the first end 103 of the tulip 101 to a terminal end 115 of the rod 110 itself, which is distal to the tulip 101.

In this situation, the longitudinal edges 114 of the rods 110 face each other and are spaced apart from each other to define an open access area 116 for accessing the above-mentioned channel 11.

Therefore, two open areas 116 are formed between the two rods 110 that extend along the cylindrical extension plane on which the outer surfaces 113 lie.

A thread 117 is also, preferably, provided formed on the concave inner faces 112 of the rods 110 near the tulip 101.

In more detail, the thread 117 also extends along a cylindrical inner surface 102a of the side wall 102. As can best be seen from the cross-section views in FIGS. 3a and 4a, the cylindrical inner surface 102a and the concave inner faces 112 are adjacent and seamless.

In addition, there are, advantageously, two weakening lines 118 each extending between an elongated rod 110 and the side wall 102. The weakening lines 118 define a separation area between the rod 110 itself and the tulip 101, i.e. an area where, as a result of a buckling of each rod 110 in relation to the tulip 101, it is possible to separate the rods 110 from the rest of the surgical screw 1.

For this purpose, the weakening lines 118 consist of grooves extending transversely to the longitudinal extension of the rods 110 and are formed on the corresponding outer surfaces 113 of the rods 110.

The grooves, thus, define a reduction in the thickness of the rod 110 such that it can be disjoined from the tulip 101 if subjected to buckling. Once the surgical screw 1 has been positioned and correctly engaged in the bone tissue, the rods 110 that project outside the patient's body, are advantageously bent by the operator to remove them.

This invention also refers to a device 2 for implanting the surgical screw 1 described above.

The device 2, better illustrated in FIGS. 5 and 6a through 6c, comprises a shaped tip 201 for engaging at the second end 108 of the threaded shank 106 to rotate the shank 106 about its longitudinal extension axis. This rotation causes the screw 1 to be screwed into the bone tissue wherein the screw 1 is to be implanted.

Figure 1:
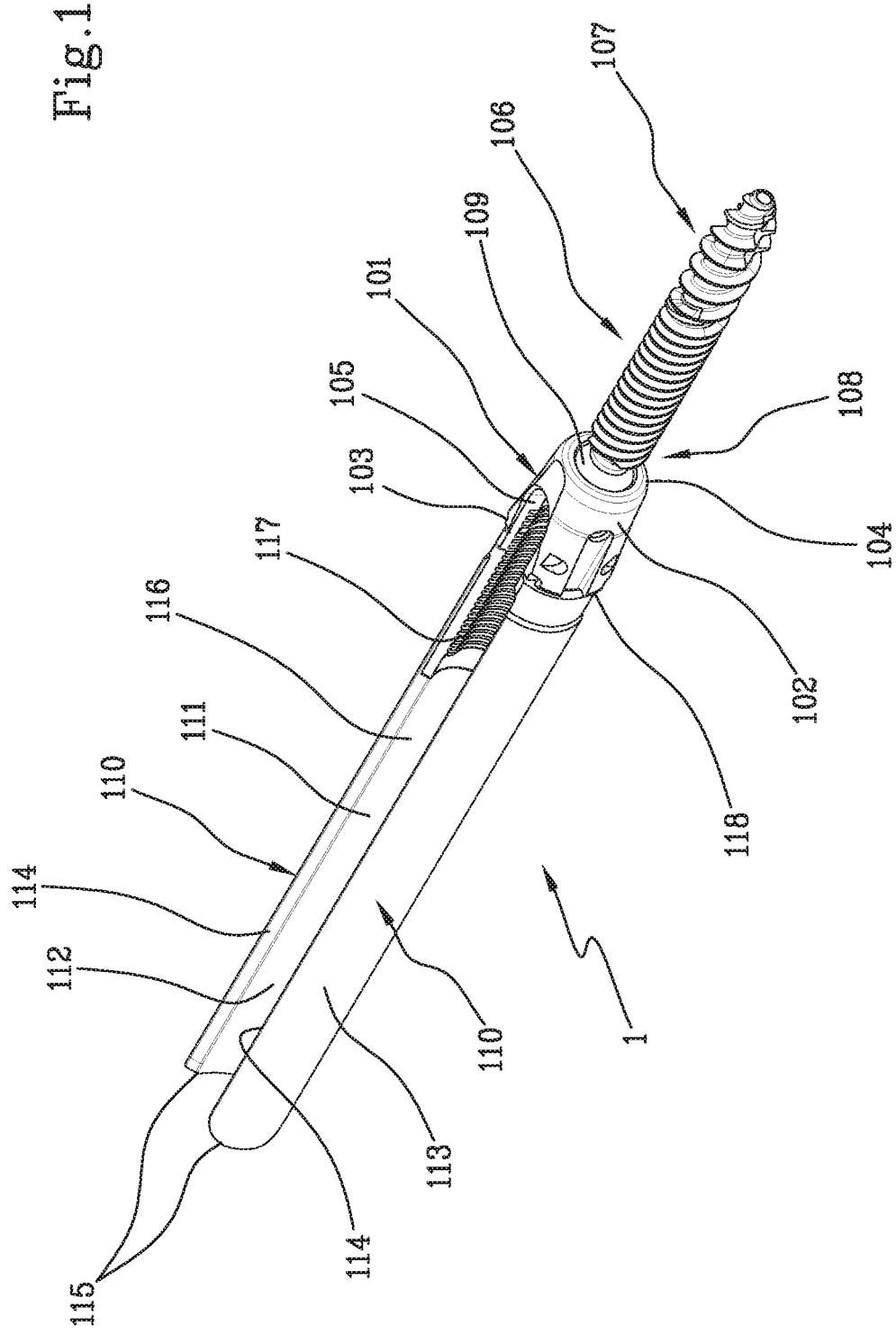
FIG. 1 is a perspective view of the polyaxial surgical screw according to this invention.
Figure 2:
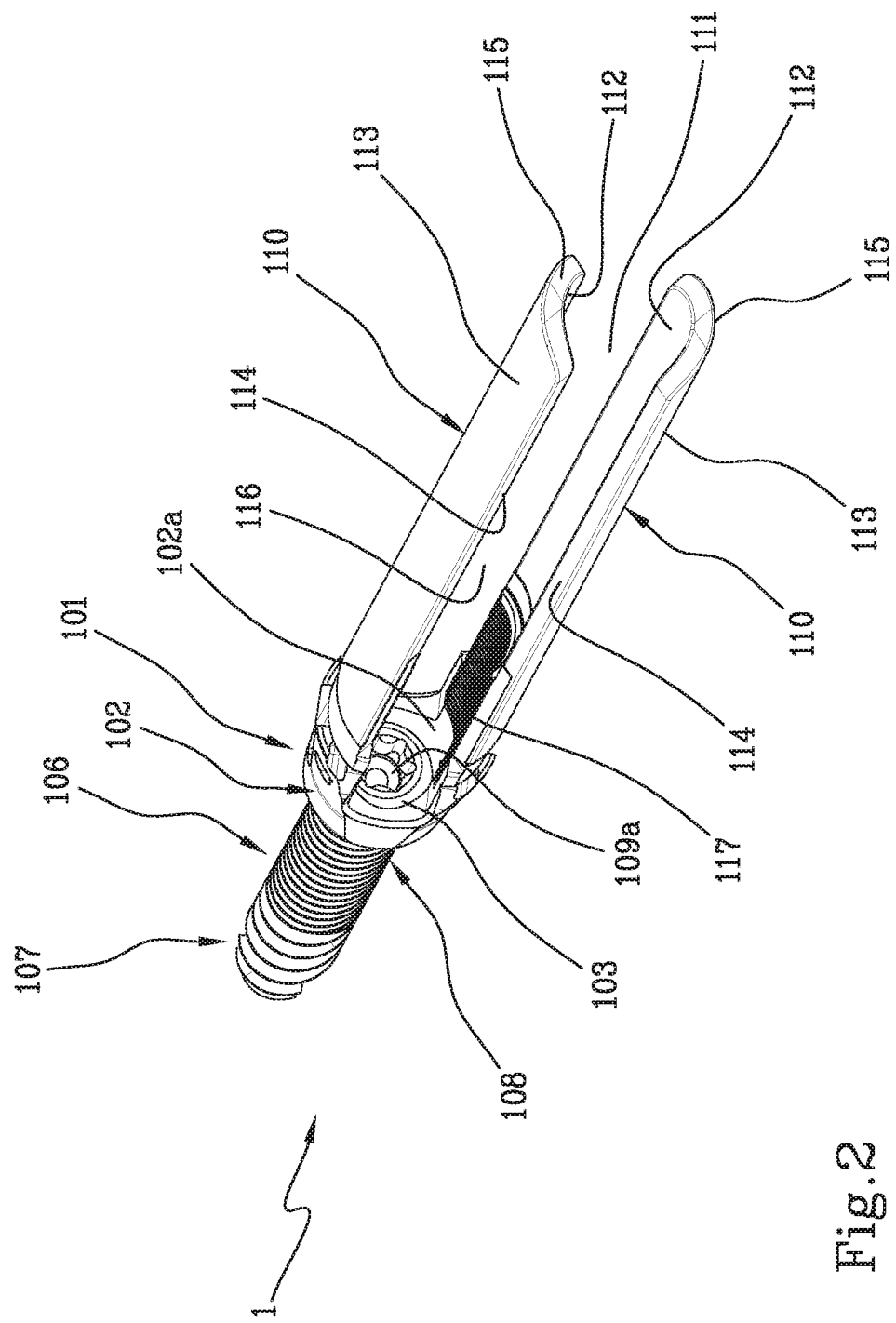
FIG. 2 shows a second perspective view of the screw in FIG. 1.

In particular, the shaped tip 201 has a head 201a of the "torx" type that can be inserted into a corresponding shaped seat 109a formed inside the ball joint 109 (more visible in FIG. 2).

The device 1 also comprises a tubular body 202 with a first end 202a to support the shaped tip 201 and a second end 202b opposite the first 202a and configured to remain outside of a patient's body.

The device 1 also has a rotation component 203 of the shaped tip 201, extending along the tubular body 202 and configured to enable manual action by the operator to tighten the screw 1.

In more detail, the tubular body 202 has at least one housing cavity 204 configured to engage the rod 110 of the surgical screw 1.

Two, spaced apart housing cavities 204 are provided, each of which is preferably configured to engage a corresponding elongated rod 110 of the surgical screw 1.

The cavities 204 are spaced apart by two corresponding arched walls 205, with elongated profiles, that are basically the same size as the rods 110 of the screw 1.

As better illustrated in FIGS. 6a and 6b, the cavities 204 are designed to accommodate the rods 110 to define a coupling between the device 2 and screw 1.

In this situation, each arched wall 205 has two longitudinal edges 205a that can abut the longitudinal edges 114 of the elongated rods 110.

In the interlocking configuration between the walls 205 and the rods 110 illustrated in FIGS. 6b and 6c, the arched walls 205 define, in collaboration with the outer surfaces 113 of the elongated rods 110, a continuous cylindrical surface 206 with a circular cross-section.

The arched walls 205 also have corresponding end portions defining the first end 202a of the tubular body 202.

These end portions support a collar 207 with a sliding hole for the above-mentioned shaped tip 201. In this way, the collar 207, rigidly supported by the walls 205, guides and supports the tip 201 that axially slides and rotates inside the collar 207.

The rotation component 203 preferably comprises an actuation cylinder 208 extending through the tubular body 202 and rotating inside the body 202 itself.

The cylinder 208 is engaged to the tip 201 (as better illustrated in the cross-section view in FIG. 6d) to rotate the tip 201 itself in an engagement configuration of the threaded shank 106.

In other words, the rotation of the cylinder 208 about its longitudinal axis determines the rotation of the tip 201 to screw the shank 106 of the screw 1 to the bone tissue.

It should also be noted, again from FIG. 6d, that the tip 201 also slides axially in relation to the cylinder 208.

In addition, the rotation component 203 comprises a bush 209 with an outer surface 210 at least partially threaded.

The bush 209, made in the shape of a hollow cylinder (FIG. 6d), is also arranged inside the tubular body 202 and is designed to house the above-mentioned actuation cylinder 208.

The threaded surface 210 of the bush 209 is formed near the tip 201 and is configured to engage the thread 117 made on the concave inner faces 112 and screw inside the rods 110.

In this situation, the actuation cylinder 208, extending inside the bush 209, is also bound to the bush 209 itself along a common longitudinal axis, while it is free to rotate relative to the bush 209.

In other words, the bush 209 and the cylinder 208 can rotate independently but are axially bound to slide towards/away from the screw 1.

In the condition (FIGS. 6b and 6d) wherein the device 2 is engaged to the screw 1, the bush 209 is advantageously screwed to the thread 117 in order to gradually advance the shaped tip 201 towards the ball joint 109 of the shank 106.

In this way, the head 201a is gradually inserted, in a controlled and precise manner, inside the seat 109a.

In addition, the rotation component 203 has an annular sleeve 211 arranged on the outside of the tubular body 202 at the corresponding second end 202b. The sleeve 211 is advantageously engaged to the bush 209 to rotate in relation to the tubular body 202 and define the rotation of the bush 209.

The sleeve 211 preferably has an ergonomic shape so that it can be better grasped by the operator who manually engages the bush 209 to the thread 117 formed on the screw 1.

The actuation cylinder 208 comprises a gripping portion 212 projecting outside the second end 202b of the tubular body 202 and also configured to be grasped by an operator.

In addition, the gripping portion 212 can be coupled with a handle (usually T-shaped) to assist the operator in positioning the threaded shank.

In this situation, it should be noted that, once the head 201a has been inserted into the seat 109a of the screw 1, the operator, acting on the gripping portion 212, screws the shank 106 into the bone tissue.

With reference to FIGS. 7a and 7b, the retaining element 3 is engaged to the polyaxial surgical screw 1 only after the implant of the screw 1 actuated by the device 2 described above.

In particular, the element 3 is internally hollow to house the rods 110 of the screw 1 and engage them inside the element 3 itself.

The element 3, which projects outside the patient's body in use, preferably has a cylindrical outer surface 301 configured to be held manually by an operator.

The element 3 has a tubular conformation and, in cross-section, preferably a basically rectangular shape with corresponding smaller faces 302 rounded outwards.

On the above-mentioned smaller faces 302 there are openings 303 designed to lighten the structure of the element 3 and to enable the screw to be seen when inserted into the rods 110 (FIG. 7a).

The smaller faces 302 have corresponding inner faces 304 with an arched and concave cross-section.

These inner faces 304 are designed to abut the convex outer surface 113 of a corresponding elongated rod 110.

Operation

The screw 1 is first engaged with the device 2 by inserting the corresponding rods 110 into the cavities 204 defined between the walls 205 (FIG. 6a). This operation ensures correct engagement of the device to the screw 2 guided by the extension of the elongated rods 110. The entire screw 1 is, therefore, correctly aligned with the extension of the device 2.

At this point, the bush 209 is rotated through the sleeve 211; thus, the bush 209, when screwed to the thread 117, brings the shaped tip 201 near the threaded shank 106. Again, the action of approaching the tip 201 is stably and precisely aligned with the screw 1.

Once the head 201a has been inserted into the seat 109a of the ball joint 109, the operator rotates the tip 201 by acting on the gripping portion 212 of the cylinder 208. In this way, the shank 106 is screwed to the bone tissue until it reaches the desired positioning. When the screw 1 has been fixed, the device is pulled out, rotating the bush 209 on the opposite side to disengage it from the thread 117. In this way, the tubular body 202 is pulled out of the elongated rods 210 of the screw 1 until the device 2 is completely disengaged.

In addition, the retaining element 3 can be inserted by fitting the elongated rods 210 inside the element 3 itself. Subsequently, once a correction rod (not illustrated) has been inserted, the operator can handle the retaining element 3 to arrange the tulip 101 by orienting it, thanks to the retaining element 3 that projects outside the patient's body. Locking threaded bushes (not illustrated) can, thus, be inserted into the tulip 101, being designed to be screwed into the thread 117 to anchor the above-mentioned rod.

Once the rod is locked, the element 3 is pulled out of the rods 110 and the rods are separated from the tulip 101 by breaking along the weakening lines 118. In particular, the separation of the elongated rods 110 is actuated by bending the rods 110 themselves in relation to the tulip 101. In this way, the weakening lines 118 enable the rod 110 to be easily broken thus enabling the extraction of the rods 110 and leaving only the tulip 101 and the threaded shank 106 inside the patient's body.

Those skilled in the art will immediately appreciate how this invention advantageously achieves the purposes listed above and overcomes the drawbacks, as described, of the prior art.

Numerous changes may be made to the form of the invention described herein and illustrated merely by way of non-limiting example, without thereby departing from the scope of protection of this invention and, thus, from the domain of this industrial patent.

The invention claimed is:

1. A system comprising:
    a polyaxial surgical screw, said polyaxial surgical screw having an internally hollow tulip having a first open end for accessing inside the tulip, a second end opposite to the first end, a side wall extending between the first and the second end, and at least two elongated rods projecting from the side wall and extending from the first end in a direction opposite to the second end, said polyaxial surgical screw having a threaded shank having a first end defining a tip of the polyaxial surgical screw and a second end opposite to the first end having a ball joint joined to the second end of the tulip to orient said shank with respect to the tulip itself, wherein said rods have respective concave inner faces facing each other, and a thread is formed on the concave inner faces of the rods near the tulip and on a cylindrical inner surface of the side wall; and
    an implantation device comprising:
        a shaped tip for engaging the second end of the threaded shank to rotate the shank itself about its own longitudinal extension axis;
        a tubular body having a first end supporting the shaped tip and a second end opposite to the first end and configured to remain outside a patient's body, said tubular body also defining at least one housing cavity configured to engage an elongated rod of said at least two elongated rods of the polyaxial surgical screw; and
        a rotation component of the shaped tip, extending along the tubular body and configured to be actuated by an operator;
    wherein said tubular body comprises two housing cavities configured to engage said elongated rods of the polyaxial surgical screw, said cavities being spaced apart by two corresponding arched walls, each-arched wall having two longitudinal edges which can abut with longitudinal edges of the elongated rods, said arched walls defining, in cooperation with outer surfaces of the elongated rods, a continuous cylindrical surface with a circular cross-section,
    wherein each arched wall comprises an end portion that defines the first end of the tubular body, said first end of the tubular body comprising a collar, wherein at least a portion of the collar is disposed radially inward from the arched walls, the collar defining a sliding hole configured to receive said shaped tip,
    wherein said rotation component comprises an actuation cylinder extending through the tubular body and rotating inside the body itself, said cylinder being engaged at the tip to rotate the tip itself in an engagement configuration of the threaded shank,
    wherein said rotation component further comprises a bush having an outer surface that is at least partially threaded, said bush being housed inside the tubular body and defining a longitudinal through cavity for housing said actuation cylinder, said threaded surface of the bush being configured to be screwed onto the thread formed on concave inner faces of the elongated rods and on the inner cylindrical surface of the polyaxial surgical screw, and
    wherein said bush is attached to the actuation cylinder along a common longitudinal axis and is rotatable relative to the cylinder about said common longitudinal axis.

2. The system according to claim 1, wherein the elongated rods are parallel and spaced from each other, said rods defining a channel in communication with the first end for accessing inside the tulip.

3. The system according to claim 2, wherein each rod has a "C"-shaped cross-section and said rods have respective outer convex surfaces opposite to the concave faces, said outer surfaces lying along a respective cylindrical extension plane with a circular cross-section.

4. The system according to claim 3, wherein the longitudinal edges extend from the first end of the tulip to a terminal end of each respective rod itself, each longitudinal edge of a first rod facing the longitudinal edge of a second rod and defining an open access area to said channel.

5. The system according to claim 3, said cylindrical inner surface of the side wall and said concave inner faces of the rods being adjacent and seamless.

6. The system according claim 2, wherein the polyaxial surgical screw also comprises two weakening lines, each of which extends between an elongated rod and the side wall to define a separation area between the rod itself and the tulip.

7. The system according to claim 6, wherein each weakening line comprises a groove extending transversely to the longitudinal extension of the rod and formed on the outer surface of the corresponding rod, said groove defining a reduced thickness of the rod.

8. The system according to claim 1, wherein said rotation component comprises an annular sleeve arranged on an outside of said tubular body at the corresponding second end, said sleeve engaging and rotating the bush and configured to be grasped by an operator, and said actuating cylinder comprises a gripping portion projecting from the second end of the tubular body and is configured to be grasped by an operator.

9. A kit comprising the system according to claim 1, wherein the kit further comprises an internally hollow retaining element configured to house said at least two elongated rods and to engage said at least two elongated rods inside the retaining element itself, said retaining element having a cylindrical outer surface configured to be manually held by an operator.

10. The kit according to claim 9, wherein said retaining element has a tubular conformation, which is internally provided with a pair of inner faces having an arched and concave conformation in cross-section, each surface being configured to abut with an outer convex surface of a corresponding elongated rod.

* * * * *